(12) United States Patent
Griner et al.

(10) Patent No.: US 6,872,545 B2
(45) Date of Patent: Mar. 29, 2005

(54) MICROBIOLOGICAL ANALYZER USING COLORIMETRIC MEANS FOR BIOCHEMICAL COLOR AND GROWTH DETERMINATIONS

(75) Inventors: Christopher Dallas Griner, Antelope, CA (US); Thomas Kenneth McDowell, Vacaville, CA (US)

(73) Assignee: Dade Behring Inc., Deerfield, IL (US)

( * ) Notice: Subject to any disclaimer, the term of this patent is extended or adjusted under 35 U.S.C. 154(b) by 126 days.

(21) Appl. No.: 10/393,478

(22) Filed: Mar. 20, 2003

(65) Prior Publication Data

US 2004/0185552 A1 Sep. 23, 2004

(51) Int. Cl.[7] .................................................. C12Q 1/20
(52) U.S. Cl. ............................ 435/33; 435/34; 435/40; 435/287.4; 435/288.7
(58) Field of Search ............................ 435/33, 34, 40, 435/287.4, 288.7

(56) References Cited

U.S. PATENT DOCUMENTS

| | | | |
|---|---|---|---|
| 4,101,383 A | 7/1978 | Wyatt et al. ............. | 195/103.5 |
| 4,236,211 A | 11/1980 | Arvesen ..................... | 364/413 |
| 4,448,534 A | 5/1984 | Wertz et al. ................ | 356/435 |
| 4,453,220 A | 6/1984 | Flegal et al. ................ | 364/413 |
| 4,643,879 A | 2/1987 | Hanaway .................... | 422/104 |
| 4,676,951 A | 6/1987 | Armes et al. ................ | 422/65 |
| 4,681,741 A | 7/1987 | Hanaway .................... | 422/100 |
| 5,580,784 A | 12/1996 | Berndt .................... | 435/288.7 |
| 5,593,854 A | 1/1997 | Berndt ........................ | 435/31 |
| 5,629,169 A | 5/1997 | Izraelevitz ................... | 435/32 |
| 5,645,800 A | 7/1997 | Masterson et al. ........... | 422/65 |
| 5,965,090 A | 10/1999 | Fanning et al. ............... | 422/65 |
| 6,086,824 A | 7/2000 | Fanning et al. ............... | 422/65 |
| 6,096,272 A | 8/2000 | Clark et al. ................... | 422/64 |
| 6,372,485 B1 | 4/2002 | Clark et al. ............. | 435/288.7 |

*Primary Examiner*—David A. Redding
(74) *Attorney, Agent, or Firm*—Leland K. Jordan

(57) ABSTRACT

A microbiological analyzer for performing ID tests on samples using colorimetric techniques to generate a pixel-wise colored map of a test region of interest and also performing MIC tests on samples using nephelometric techniques to determine which antimicrobial agents are most effective against a particular microorganism.

17 Claims, 2 Drawing Sheets

MICROBIOLOGICAL ANALYZER USING COLORIMETRIC MEANS FOR BIOCHEMICAL COLOR AND GROWTH DETERMINATIONS

FIELD OF THE INVENTION

The present invention relates to an automated microbiological analyzer for determining both the identity of a microorganism and the concentration of an antibiotic effective in inihibition of growth of the microorganism. More particularly, the present invention provides a microbiological analyzer with the ability to use colorimetric and chromogenic means in determining the identity of different microorganisms and colorometric means in determining microorganism presence.

BACKGROUND OF THE INVENTION

Various types of tests related to patient diagnosis and therapy can be performed by analysis of a biological sample. Biological samples containing the patient's microorganisms are taken from a patient's infections, bodily fluids or abscesses. Microorganisms from these samples are typically placed in test panels or arrays, combined with various reagents, incubated, and analyzed to aid in treatment of the patient. Biochemical analyzers have been developed to meet the needs of health care facilities and other institutions to facilitate analysis of patient samples and to improve the accuracy and reliability of assay results when compared to analysis using manual operations.

An important family of microbiological analyzers function as a diagnostic tool for determining both the identity of an infecting microorganism and of an antibiotic effective in inhibition of growth of the microorganism. In performing these in vitro tests, identification and antibiotic susceptibility patterns of microorganisms isolated from biological samples are ascertained. Such analyzers place a small sample to be tested into a plurality of small sample test wells in panels or arrays that typically contain different enzyme substrates or antimicrobics in single or serial dilutions. Identification (ID) of microorganisms and determination of Minimum Inhibitory Concentrations (MIC) of an antibiotic effective against the microorganism are determined by color changes or the degree of cloudiness (turbidity) in the sample test wells created in the arrays. By examining the signal patterns generated, both MIC and ID determination and subsequent analysis are performed by computer controlled microbiological analyzers to provide advantages in reproducibility, reduction in processing time, avoidance of transcription errors and standardization for all tests run in the laboratory.

In ID testing of a microorganism, a standardized dilution of the microorganism sample, known as an inoculum, is first prepared in order to provide a cellular suspension having a concentration within a predetermined range. This inoculum is placed in an analytical test array or panel having a number of wells. The test wells contain predetermined identification media consisting of enzyme substrates or antibiotics, which, depending on the species of microorganism present, will exhibit color changes or increases in turbidity after incubation. For instance, bacterial genera may be identified on the basis of pH changes, its ability to utilize different carbon compounds, or growth in the presence of antimicrobial agents in a test well. Some tests require addition of reagents to detect products of microorganism metabolism while others are self-indicating. In conventional chromogenic and colorimetric panels, the inoculum is incubated for a period of time before analysis is completed. By examining the reaction of the inoculum and reagents after incubation and comparing that reaction with that of known species, the types of microorganisms can be identified. Importantly, a large number of different substrates or other reagents must be available in ID testing of an unknown microorganism because the microorganism will be more or less sensitive to different substrates and reagents. This may be achieved by providing a variety of ID test panels, each pre-loaded with substrates and reagents that are selected to produce a known pattern of measurable reaction signals for various microorganisms.

The use of microbiological test panels and the techniques employed in antibiotic susceptibility testing, AST, of microorganisms, in order to determine their MIC, is well known. AST tests are tests using wells filled with inoculum and a growth broth, called herein an inoculum-broth solution, and increasing concentrations of a number of different antibiotics as used in different AST tests to determine which antimicrobial agents are most effective against a particular microorganism. The different antimicrobial agents are typically diluted in Mueller-Hinton broth with calcium and magnesium in colorimetric panels. The antimicrobials are diluted to concentrations that include those of clinical interest. AST testing requires that the test trays be incubated at a controlled temperature for a period of time so that an observable change in the number of cells has a chance to occur. Each well of the test tray is then examined for changes in turbidity. The analyzer compares each test well reading with a threshold value. The threshold value is a fixed number corresponding to a certain percentage of relative absorbency that corresponds to clinically significant growth. These changes are interpreted using a variety of methods to identify the minimum inhibitory concentrations of various antibiotics for different microorganisms.

Analyzers that carry out multi-step biochemical analytical procedures in an automated or semi-automated fashion are well known. For example, microbiological analytical systems currently carry out automated MIC procedures using both photometric and fluorometric detection methods. The MicroScan Division of Dade Behring Inc. sells a device of this type under the trade designation WalkAway® analyzer. Armes et al. U.S. Pat. No. 4,676,951, Hanaway U.S. Pat. Nos. 4,643,879 and 4,681,741, and Masterson et al. U.S. Pat. No. 5,645,800 describe certain features of the WalkAway® analyzer. Prior commercial embodiments of the Walk-Away system analyze panels carrying microbiologic samples. Automated features of more recent microbiological testing machines are well known in the art, having been described in the following patents from which it may be seen that functions such as automated handling and transport of test devices like panels or rotors throughout an analyzer are well known. Those skilled in the art have a variety of well-known techniques and choices for the routine tasks of test device transport, optical testing, computer control, etc., as described in a number of U.S. Patents, for instance, the biochemical analyzers and ID and MIC techniques described in the following U.S. Pat. Nos. 3,928,140; 3,957,583; 4,101,383; 4,236,211; 4,448,534; and 4,453,220.

More recently, advances have been made in the art of microbial MIC and ID testing, including use of advanced light sources, and use of improved methods to enhance the accuracy of the ID and MIC determinations.

U.S. Pat. No. 5,580,784 discloses the use of chemical sensors to determine whether a particular test well is evidencing bacterial growth by directing radiation sources having closely spaced wavelengths into the well. Emissions from the chemical sensor due to the two spectrally spaced radiation sources are monitored, and a ratio of their differences and sums is calculated in order to minimize station-to-station variation between the radiation sources or detectors, and lot-to-lot variations in the sensor materials.

U.S. Pat. No. 5,593,854 discloses a method of analyzing data from a fluorescent chemical sensor by calculating a ratio based on the AC and DC components of the emission from the sensor. This ratio, or the emission modulation, changes if bacterial growth is ongoing in the test well. By focusing the desired ratio into a high resolution area, and adjusting the frequency until the system reaches that ratio, one ensures that all readings are performed at a high resolution area of the sensor. The adjusted frequency is utilized to provide an indication of whether the particular vial is experiencing bacterial growth.

U.S. Pat. No. 5,629,169 estimates drug effectiveness from a drug diffusion sample including a plate having a medium containing a test organism and a plurality of antibiotic disks positioned on the plate in a medium. An inhibition zone surrounds each of the antibiotic disks after incubation. The drug diffusion sample is illuminated, and an image of the drug diffusion sample is acquired with a video camera. The image is analyzed by determining the locations of the antibiotic disks, determining the average brightness and the brightness variance of the image in a region surrounding each of the antibiotic disks, and estimating the radius of the inhibition zone surrounding each of the antibiotic disks from the average brightness and the brightness variance. The radius of the inhibition zone is indicative of drug effectiveness.

U.S. Pat. No. 5,965,090 provides an automatic sample testing machine for testing samples stored in test cards. The machine has a test sample positioning system for moving a tray containing a plurality of test sample cards and fluid receptacles among various stations in the machine. The machine has a diluting station for adding a predetermined quantity of diluent to the receptacles. A test card transport station transports the test cards from an incubation station to an optical reading station, where transmittance and fluorescence optical testing is conducted.

U.S. Pat. No. 6,086,824 discloses an automatic sample testing machine for testing samples stored in test cards. The test sample cards are placed in a tray and a transport station transports the tray from the incubation station to an optical reading station, where the cards are removed from the tray and optical measurements (e.g., transmittance and/or fluorescence optical testing) are conducted on test wells within the card. The machine has a sample loading station where test samples are placed in fluid communication with test cards in the trays.

U.S. Pat. No. 6,096,272 discloses a diagnostic microbiological testing system and method for microorganism identification (ID) and antimicrobial susceptibility determinations (AST). The system includes multiple-well test panels capable of performing ID and AST testing on the same test panel. Each test panel is inoculated with reagents, broth-suspended organisms, and placed into the instrument system. The instrument system includes a rotating carousel for incubation and indexing, multiple light sources each emitting different wavelength light, colorimetric and fluorometric detection, barcode test panel tracking and a control processor for making determinations based on measured test data.

U.S. Pat. No. 6,372,485 provides for both microorganism identification (ID) and AST determinations. The system includes multiple-well test panels capable of performing ID and AST testing on the same test panel. Each test panel is inoculated with reagents, broth-suspended organisms, and placed into the instrument system. The instrument system includes a rotating carousel for incubation and indexing, multiple light sources each emitting different wavelength light, precision colorimetric and fluorometric detection, barcode test panel tracking and a control processor for making determinations based on measured test data. One light source includes a plurality of LEDs arranged in a linear array. Each of the LEDs junction currents is controllable to produce a predetermined illumination profile.

From this discussion of the art state in automated microbiological analyzers, it may be seen that current microbiological analyzers frequently employ complex optical or similar techniques in order to determine density patterns of samples corresponding to ID test wells and compare those patterns to predetermined ID patterns in order to be capable of accurately performing ID testing on an unknown microorganism. However, known state-of-art analyzers are generally employing measurement techniques in which signals are assigned a positive or negative value depending on whether or not a microorganism has or has not either produced a biochemical reaction that changes a test solution's color or has or has not grown in the presence of certain antimicrobial agents. Such a "has or has not" approach to ID is susceptible to errors because of the uncertainty of establishing precise cut-off range limits between positive or negative values resulting in an unwanted degree of uncertainty or inaccuracy in ID testing.

SUMMARY OF THE INVENTION

The present invention meets the foregoing need for improved accuracy in obtaining accurate microorganism identification by using colorimetric and chromogenic techniques to generate a pixilated color-value map of a test region of interest. An exemplary embodiment of the present invention may be practiced in an automated microbiological analyzer in which a test panel designed for performing ID and MIC tests has been previously prepared and incubated is placed. The test panel and the tests to be performed are identified to a computer programmed to appropriately operate the analyzer. The test panels are variously preloaded with substrates, reagents, growth media and antibiotics that have been predetermined to produce a known pattern of measurable colorimetric or photometric signals that may be correlated to various known microorganisms. The analyzer completes the requested tests by means of panel transport stations and colorimetry and nephelometry analysis stations to generate a pixelized map of each test well with minimal clinician attention.

Colorimetry measures color by measuring the interaction of a sample with known light sources by aligning a detector to the axis of an incident light source and measuring the absorbance caused by the well. Nephelometry measures the ability of the microorganism cells to scatter light by aligning a detector at an angle to the axis of that of an incident light source and are significantly more sensitive than conventional turbidity measurements.

BRIEF DESCRIPTION OF THE DRAWINGS

These and other features and advantages of the present invention can best be understood by reference to the detailed description of the preferred embodiments set forth below taken with the drawings in which.

DETAILED DESCRIPTION OF THE PREFERRED EMBODIMENTS

Figure 1:
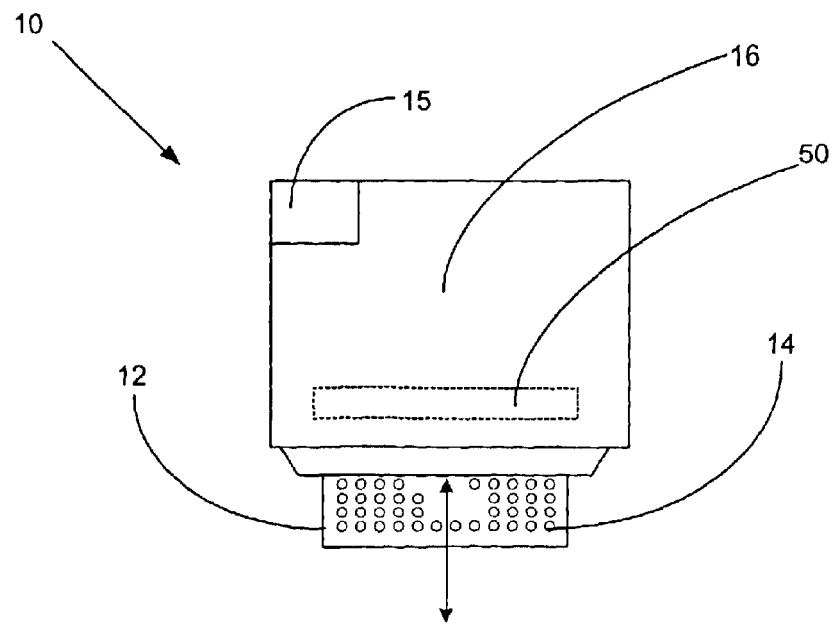
FIG. 1 is a simplified plan view of a portion of a microbiological analyzer in which the present invention may be practiced.

FIG. 1 schematically illustrates a microbiological analyzer 10 illustrative of an analyzer in which the present invention may be practiced, the analyzer 10 having at least one specimen panel 12 carrying previously prepared suspensions of microbiologic biochemicals in a plurality of wells 14. Using known techniques and electromechanical devices, like those disclosed in U.S. Pat. No. 5,645,800, assigned to the assignee of the present invention, analyzer 10 is adapted to transport specimen panel 12 into and away from a measurement station 16, as indicated by a double arrow, under control of a central microprocessor 15 preprogrammed to perform a number of analytical ID and MIC test protocols.

In an embodiment illustrative of the recent invention, measuring station 16 detects and quantifies the presence of microorganisms and detects and quantifies the color of the fluid in wells 14 of specimen panel 12. As described later, measuring station 16 measures microorganism growth using calorimetric and nephelometric techniques. Specimen panel 12 is typically a plastic 96 well microdilution, or microtiter tray, about 10 cm×13 cm×1.5 cm, and contains either biochemical substrates used for microorganism identification (ID), or dilutions of antimicrobial agents for determining minimum inhibitory concentrations (MIC), or both. Specimen panel 12 typically has 8 rows of wells 14 from top to bottom and 12 columns of wells 14 from left to right. Each well 14 in specimen panel 12 can be thought of as a small test tube capable of containing about 300 microliters of biochemical liquid comprising some combination of biochemical reagents, indicators, various concentrations of antibiotics, growth media, and the organism under test. Specimen panels 12 are single-use, disposable, inert plastic trays wherein the plastic material can be light transmissive to permit analysis of the specimens by photometry.

ID tests in conventional colorimetric and chromogenic panels are based on the detection of pH changes, substrate utilization, and growth in the presence of antimicrobial agents after 18–24 hours of incubation. Each organism to be identified possesses a set of enzymes that act as chemical catalysts or fermentors. By performing a series of chemical reactions in a medium where an unknown organism is growing, it is possible to identify a combination of positive and negative reactions that effectively provide an identifying chemical fingerprint for that previously unknown organism. Typically, these reactions include fermentation of a wide range of carbohydrates, citrate utilization, malonate utilization, phenylalanine deaminase production, beta galactosidase production, indole production, hydrogen sulfide production, lysine decarboxylase production, ornithine decarboxylase production, urease production, sucrose utilization, and arginine dehydroxylase production. A reaction result is determined by a color change in the medium. The color causing reagent in most cases is a pH indicator which measures the alkalinity or acidity resulting from the chemical reactions. A variety of indicators such as bromphenol blue and phenol red may be used to measure pH changes over a wide range of the pH scale. Another mechanism for chemical color development is the enzymatic splitting of a chromogen (color producing chemical) off the original substrate, thus signaling a positive chemical reaction. A combination of color reactions as just described forms a profile that may be used to identify by standard statistical methods the probability of each organism occurring for each combination of detected colored chemical reactions.

Figure 2:
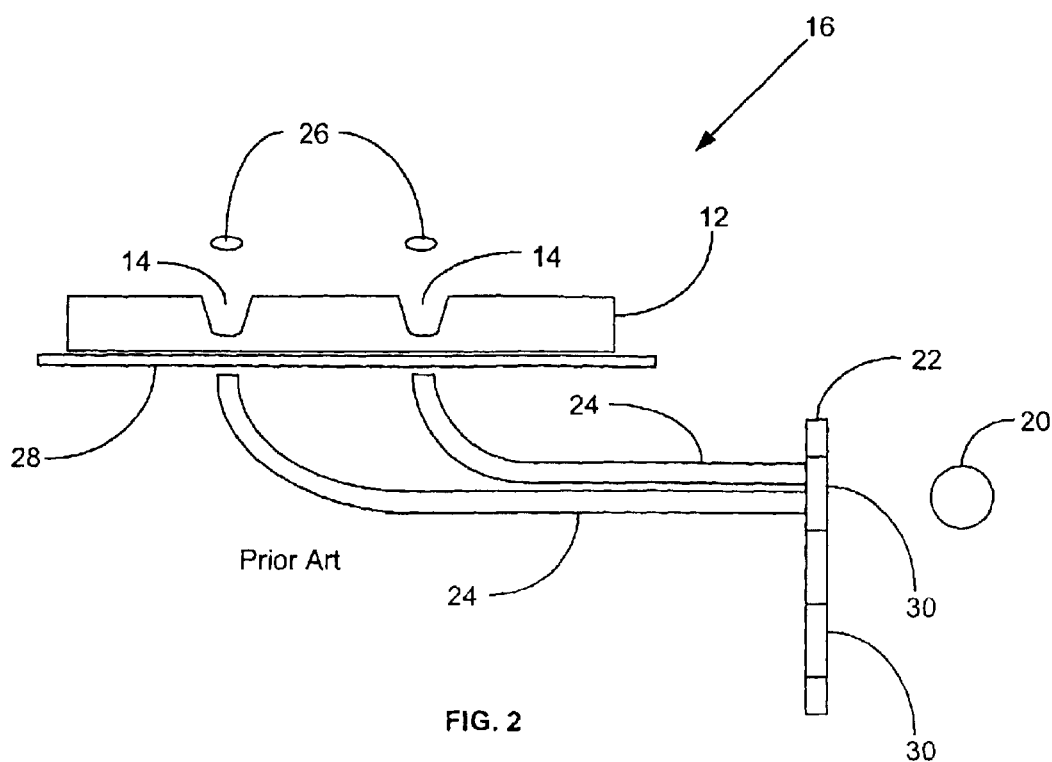
FIG. 2 is a simplified schematic view of typical prior art measuring system; and, FIG. 3 is a schematic elevation view of the measuring system of the present invention.

Prior art measuring stations 16, like seen in FIG. 2, for determining MIC align each individual well 14 in specimen panel 12 with an interrogating optical beam of radiant light generated, for example, by an incandescent tungsten-halogen lamp 20. The interrogating beam of light is directed through a multi-filter mechanism 22 and then guided by optic emitter lines 24 through each well 14 onto photodiode detectors 26. Optic emitter lines 24 are arranged in a grid spaced apart relationship, below panel 12. The distance between next adjacent optic emitter lines 24 corresponds with the distance between next adjacent wells 14 within panel 12. A multi-position aperture plate 28 located between fiber optic emitter lines 24 and panel 12 directs the interrogating beam of light to radiate or illuminate a specific portion of the well 14 with a beam of interrogating radiation. Each optic emitter line 24 may include a lens (not shown) that condenses the light beam exiting the optic fiber into a narrow vertical beam, by that maximizing the illumination of each well 14. Measurements of radiant energy transmitted through each well 14 are taken for all wells 14 in panel 12 for each of an number of different filters 30 in multi-filter mechanism 22 and aperture plate 28 positions. Measurements are typically made using photodiode detectors 26 paired with the optic emitter lines 24. The photodiode detectors 26 face the optic emitter lines 24 and measure the intensity of filtered light after its transmission through the specimens in the wells 14. Conventional calibration schemes are employed to compensate for variations in filters 30, optic emitter lines 24, photodiode detectors 26 and the like.

All of the light incident upon photodiode detectors 26 is integrated together to form a single electrical signal that is proportional to the total amount of light transmitted through each well 14. The color of each well 14 is determined by measuring the absorption of the various colors of light by the well 14. Wells 14 are perceived to be a certain color by absorbing certain parts of the visible spectrum and passing other parts. Light interrogating well 14 that is close to the color of well 14 will pass through with little change. Light interrogating well 14 at a different color will be largely absorbed. Well 14 color is inferred by looking at the response of the filters 30 for the one with the greatest output. Cellular presence in well 14 complicates this prior art method of color measurement because it tends to scatter off or absorb the light from all the filters 30, independent of the color of well 14. This complicates the algorithms, requiring the combination of data from two or three different filters 30 to determine the color state of a well 14. In addition, when narrow bandwidth filtered light is passed through well 14 and absorption is measured, adverse effects from well 14 imperfections, contaminants, precipitates and color saturation make it difficult to differentiate between a small color change and any of these adverse effects. When measuring MIC, growth aperture plate 28 is closed to force the light to pass mainly through the small flat at the bottom of well 14. The design of the well 14 typically causes growth to concentrate at the bottom of the well 14. As light passes through well 14 and hits microbic growth, light is scattered off axis and misses photodiode detector 26. The drop in signal is assumed to be proportional to the growth present. A high wavelength filter 30 is used for growth detection because although a greater response could occur at lower wavelengths of light (more absorption and scattering would take place), fluid in well 14 tends to be tinted a light brown or amber color which would absorb the lower wavelengths and be falsely interpreted as growth. Also more gain is required at the lower wavelengths due to the insensitivity of the photodiodes 26, which causes more noise. Panel imperfections will also cause light to scatter off axis and be interpreted as growth.

Figure 3:
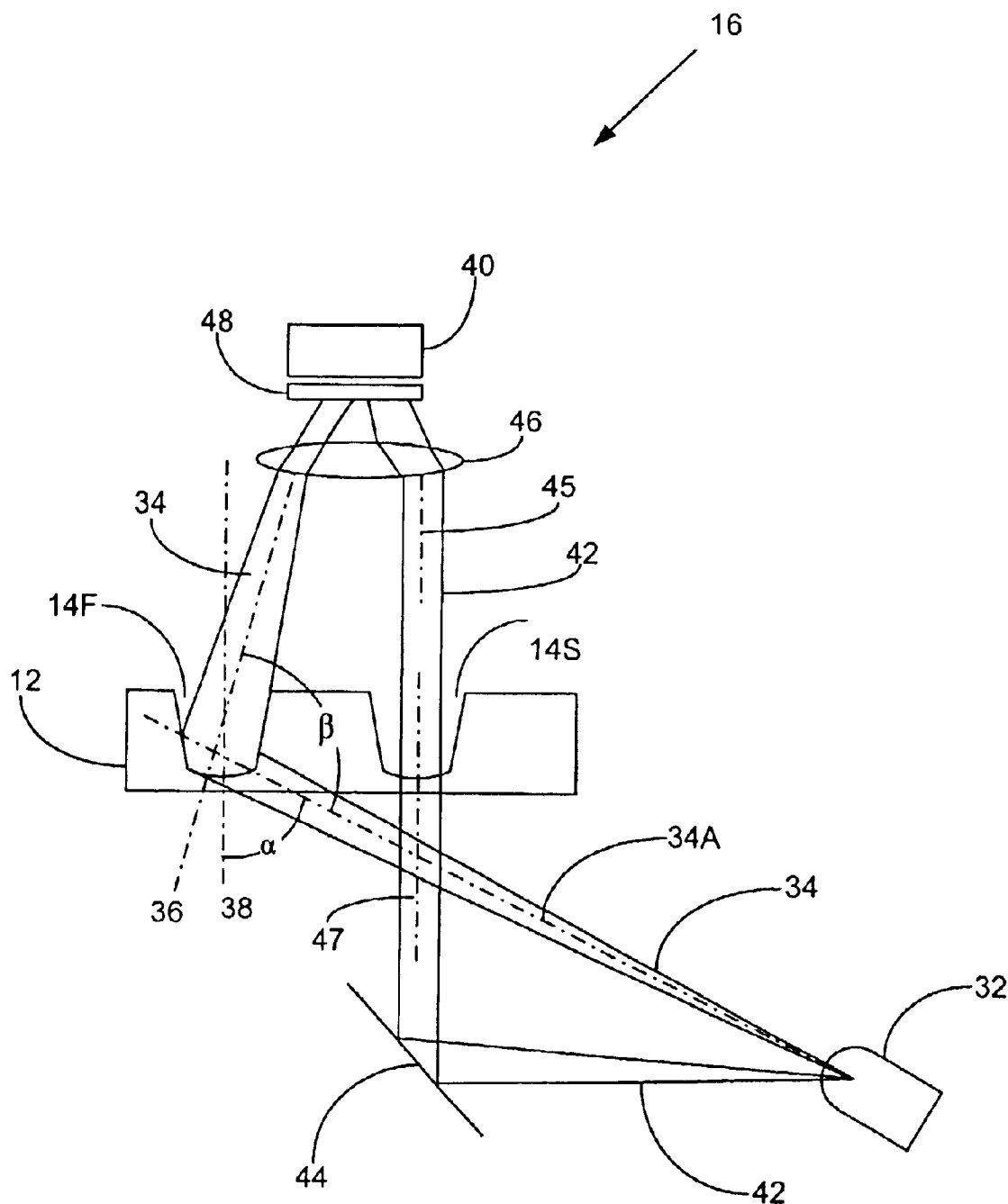

The present invention described in conjunction with FIG. 3 differs from the prior art techniques described in that the hue, saturation, and intensity of colored light measured by photodiode detector 40 after being filtered by filter 48 and fluids in sample wells 14 will be used to ascertain the color state, and thereby enabling an improved accuracy in establishing the identity of the unknown microorganism in well 14. Sample identification wells 14 in panel 12 represent specific biochemical tests and biochemical color interpretations that have been pre-determined for each of the different variations in use and makeup of panels 12. Color interpretation is not always simple because, for example, the difference between orange-red and red-orange, as is the case with carbohydrate-based reactions, is not always obvious, since in the process of changing from an initial red to a final yellow color, the color in well 14 changes through all the colors therebetween. An objective of the present invention is to eliminate the vagaries of human judgments in ascertaining the true color of fluids in wells 14 by measuring light filtered through color filters to obtain accurate hue, saturation, and intensity values of fluids in wells 14.

As seen in FIG. 3, in the present invention measuring station 16 comprises at least one white light LED 32 as the light source instead of a tungsten-halogen bulb. LEDs like LED 32 may be obtained from Agilent Technologies, identified as a Precision Optical Performance White LEDs, number HLMP-CW31. An LED 32 is seen placed in a position with respect to a first well 14F so that a first portion of the white light interrogating radiation from LED 32, indicated by the reference numeral 34 along a first optical axis 34A, enables nephelometric or off-axis measurement of light scattering from the contents of first well 14F along a second optical axis 36 not aligned with the optical axis 34A by a sensor 40. Another portion of the white light interrogating radiation, indicated by the reference numeral 42, from LED 32 is reflected from a diffuse surface 44 placed below a second well 14S, passing directly through second well 14S along a third optical axis 45 aligned with the vertical axis 47 of second well 14S to also be measured by sensor 40. The color of the light 42 passing through test well 14S will be altered by the contents of second well 14S and will be used to assess the color of second well 14S. More than one LED 32 may be used for making such nephelometric and colorimetric measurements, however for the sake of simplicity, only one is shown in FIG. 3. Similarly, a single LED 32 may be used for making such nephelometric and colorimetric measurements, however to avoid an overly complex drawing, two LEDs are shown in FIG. 3. Sensor 40 in conjunction with a dividing lens 46 divides the field of view into discrete areas called pixels that can be evaluated separately.

During sensor measurements of the amount of interrogating radiation 34 passing through first well 14F and used to ascertain MIC and during measurements of the amount of interrogating radiation 42 passing through second well 14S and used to ascertain ID, the bottom of each well 14F and 14S is divided into 2000–4000 equal sized pixels. In accord with the present invention, in the instance of ID measurements, color light readings are made by sensor 40 for each pixel, and then either averaged or formed into a histogram (binned) across well 14S to accurately arrive at a single color vector or detect the presence of a particular color vector, as explained hereinafter, for well 14S.

Color filters 48 are incorporated into sensor 40 eliminating the necessity for a multi-filter positioning assembly, thereby detecting colored light passing through well 14S and producing an array of signal values for each well 14S that can be selectively combined to produce a single color value for the well. Sensors like sensors 40 may be obtained from Agilent Technologies, identified as a CMOS Image Sensor, number ADCS-2021 or National Semiconductor, identified as a Color CMOS Image Sensor, number LM9628. Preferably, sensor 40 and lens 46 are positioned over panel 12 to obtain adequate view and resolution of bottom of well 14F and 14S. More than one sensor 40 may be used for complete panel evaluation, however for the sake of simplicity, only one is shown in FIG. 3. Three wide bandwidth filters 48 are integrated within sensor 40. One filter generally covers the blue range of the visible spectrum, another generally covers the green range and the last filter generally covers the red range, thereby selectively determining the components of the light that enters sensor 40. A key factor in the present invention is that these wide bandwidth filters 48 are selected to closely simulate the color detection mechanism of the human eye.

Panel 12 may be advantageously positioned under a sensor array 50 in FIG. 1. (shown in dashed lines) of six sensor elements 40. Each sensor element 40 will measure 2 wells 14S for color and 2 wells 14F for growth (in a 2×2 matrix) at the same position of panel 12. This enables two rows of test wells 14 in panel 12 to be read at each position of panel 12 below the sensor array 50. Mechanical drives are conventionally employed to stepwise locate panel 12 below the sensor array 50 so that the full panel may be automatically read. Each sensor array 50 will be controlled by a programmable digital signal processor in computer 15 in order to perform the data compression including pixel selection, filtering, RGB to HSI conversion, and histogram generation. The test well data from each digital signal processor is used by computer 15 or by an external computer for further processing to ascertain ID and MIC of patient samples. Computer 15 will also control the motion axis, the user interface, and communications with any external computers.

The pixel-wise digital signal measurements made by sensor 40 using the red, green, and blue filters are generally designated R, G, and B signal values, respectively. Mixing these three colors in varying proportions can reproduce any color that can result from a color-generating reaction within second well 14S in the form that a human eye can see. If red, green and blue unit vectors are orthogonally placed on a polar coordinate system, a "color wheel" is defined that contains all the visible colors. The vector addition of the R, G and B values obtained from reading the sample will produce a vector that defines the color of the sample.

Three values, hue, saturation, and intensity are used to accurately characterize any given color. Hue (H) represents the actual color and is the angle of the vector. Saturation (S) represents the intensity of the color and is the magnitude of the vector. Intensity (I) is the average of the RGB values and represents how light or dark the fluid sample in second well 14S is. The following equations can be used to convert from the RGB domain to the HSI domain[1]:

[1]CRANE, RANDY [1997]. *A Simplified Approach to Image Processing.* Upper Saddle River, N.J: Prentice-Hall, Inc.

$$H = \cos^{-1}\left[\frac{0.5[(R-G)+(R-B)]}{\sqrt{(R-G)^2 + (R-B)(G-B)}}\right] \quad \text{Formula 1}$$

if $B > G$ then $H = 360° - H$ $$S = 1 - \frac{3}{(R+G+B)}[\min(R, G, B)] \quad \text{Formula 2}$$

$$I = \frac{(R+G+B)}{3} \quad \text{Formula 3}$$

Algorithms for determining the true color of the unknown sample in second well 14S will use the H and S values. A range of angles will be defined for positive reactions and another range will be defined for negative reactions for each colorimetric test family. The H value will be compared against these ranges to determine the state of second well 14S. The S value will be used to determine if there is any color in second well 14S (S is greater than a predetermined threshold for a visible color to be present) and will also be used for clear to color reactions.

Methods to ascertain the identity of the unknown sample in panel 12, once the measured H and S values are calculated by a computer operated program within computer 15 establish the true color of second well 14S, generally employ computer-based statistical probability analyses. In such probability analyses, actual color readings made for a number of different second wells 14S containing different color-generating chromogenic reagents are compared with a database table containing the color reaction patterns of a number of known possible microorganisms. Such an analysis may be made by computer 15 or made on an external computer. In either instance, a computer-based program will interpret the true color of the unknown sample as either a positive chromogenic reaction or a negative chromogenic reaction. Computer 15 then analyzes each of the known possible microorganisms and computes its probability of occurrence.

Each of the actual probabilities of each biochemical reaction is cumulatively multiplied for each of the known sample microorganisms in the database table to obtain the net probability for each unknown microorganism. The microorganism with the highest net probability is the most likely organism. If the net probability of the most likely microorganism is less than a pre-established limit, then a warning will be issued by computer 15 or an external computer to the operator that the net probability is possibly too low, and possible technical errors should be checked. If the net probability is greater than this pre-established limit, then analyzer 10 or an external computer proceeds to normalize the test results. This is done by dividing each of the microorganisms net probabilities by the sum of all of the net probabilities. Thus, an estimate of the probabilities for the unknown microorganism relative to each of the known microorganisms is obtained.

Antimicrobial susceptibility tests (AST) are broth dilution susceptibility tests in which various antimicrobial agents are diluted in Mueller-Hinton broth with calcium and magnesium in conventional calorimetric panels. The antimicrobials are diluted to concentrations to include those of clinical interest. According to the present invention, the minimum inhibitory concentration (MIC) of each antimicrobial agent is measured using nephelometric techniques rather than previously practiced techniques detecting visible growth directly using absorbance methods.

To evaluate the presence of growth in first well 14F a histogram is calculated by computer 15 from the intensity (I) value of each pixel of first well 14F. A cluster will form towards lower values of I of the histogram that is proportional to the amount of background that is seen. A threshold will be set that will distinguish background from scatter. When the number of pixels to the background side of the threshold drops below a second threshold then a sufficient number of pixels represent scatter and therefore growth. The second threshold will be set such that scatter from well characteristics and defects, described below, will not be called growth.

Panels 12 are normally made using known plastic injection molding techniques having a pin for each well 14 in the mold. These pins form the inside of well 14 and are frequently reworked to keep them in specification as they wear. This causes each well 14 to have slight variances in plastic thickness, internal radii, and bottom diameter. In production, heated plastic is injected through gates at one side of a panel 12 and flows around the pins as it travels towards the other side of panel 12. A knit line forms where the plastic meets after it flows around the pins. If the plastic is overheated it will discolor resulting in a slight hue to panel 12. Panel ejection from the mold or panel mishandling may also result in chips or scratches in the well bottoms. Because wells 14 are pixilated during evaluation and the location of certain well characteristics is known the pixels associated with these well 14 characteristics are excluded from the histogram, another advantageous feature of the present invention.

Test panel 12 is preferably laid out in a rectangular matrix, which may comprise for example 8 rows and 12 columns of test wells 14F and/or 14S. Those first wells 14F dedicated for obtaining MIC values may be arranged such that each of the 12 columns of wells 14F contains a single antibiotic in a series of different dilutions. There may be several different concentrations of each antibiotic, with at least several wells 14F of panel 12 used for control purposes. For example, one control well 14F might be used for unrestricted growth of bacteria to confirm a proper testing cycle, and another well used to represent no growth.

A microorganism sample is distributed uniformly into first wells 14F containing the various dilutions of different antibiotics forming a sample test mixture. After an incubation period sufficient to allow detectable growth of the microorganism in first well 14F, in the event that the particular antibiotic in the particular concentration being tested does not prevent growth, a growth culture results within the sample test mixture. Growth in first well 14F appears as turbidity in the form of a white haze, a white button in the center of first well 14F or as fine granular growth and is characterized by slowly changing values from pixel to pixel. In prior art analyzer configurations, MIC readings were generally taken by a photosensor placed directly inline with the optical axis of the light source. A key feature of the present invention is that light 34 along a first optical axis 34A and emanating from LED 32 enters first well 14F as seen in FIG. 3 at an angle α not aligned with the vertical axis 38 of first well 14F and passes through the sample test mixture therein. The amount of light 34 that is scattered along second optical axis 36 at an angle β not aligned with first optical axis 34A is captured by photosensor 40 in a nephelometric detection technique. Pixels detecting this scattering will look gray. Pixels where no scattering takes place will look like the background (black).

The pixel values will be run through a low pass filter to minimize the effects of large step changes in the data which are more likely to be caused by well defects or contaminates than by microorganism growth. Thus, in the preferred embodiment of the present invention, in the instance of an MIC measurement, the intensity of the light is sensed via nephelometric techniques and converted from an analog to a digital value corresponding to the opacity of the culture. Nephelometry measures the ability of the microorganism particles to scatter light, and the detector is aligned at an angle to the optical axis of the light source. Turbidity measures the net effect of absorbance and scatter, and the transducer is aligned with the optical axis of the radiation source. Nephelometry measurements are significantly more sensitive than turbidity measurements because nephelometry measures the presence of any signal, even though small, whereas traditional turbidimetric techniques measure small signal losses in large signal values.

This opacity value representing the increase in turbidity of the sample since inoculation stems from the net effect of light scatter in first well 14F. Computer 15 or an external computer functions to correlate digital values representing, for example, bacterial growth for the various first well 14F with a particular drug. From such correlation, computer 15 or an external computer selects, for example, the zero growth indication stemming from the weakest concentration of each drug, and this concentration becomes the MIC value for that particular drug. If none of the first wells 14F containing a particular drug indicate inhibition of growth, the computer 15 or an external computer prints that the infectious organism is resistant to that particular drug.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A method for operating a microbiological analyzer adapted to perform microbiological tests on samples suspected of containing a microbial agent, the method comprising:

placing the sample and microbiological chemicals in a test well having a vertical axis and incubating the mixture;

exposing the incubated mixture to a beam of interrogating white light along a first optical axis aligned with the vertical axis of the test well;

color filtering the light passing through the incubated mixture along the first optical axis;

measuring the hue, saturation, and intensity of the color filtered light along the first optical axis; and, using the hue, saturation, and intensity of color filtered light to identify the color of the incubated mixture.

2. The method of claim 1 wherein color filtering the light passing through the incubated mixture comprises filtering the light with red, green and blue filters.

3. The method of claim 2 wherein measuring the intensity of the color filtered light comprises dividing the test well into a plurality of pixels, measuring the filtered intensity for each pixel.

4. The method of claim 3 wherein the hue, saturation, and intensity of each pixel of the incubated mixture, calculated from the measured intensities, are accumulated into a histogram or averaged to arrive at a single hue, saturation and intensity.

5. The method of claim 4 wherein the identity of a microbial agent within the sample is determined from the hue, saturation, and intensity of the incubated mixture.

6. The method of claim 1 wherein exposing the incubated mixture further comprises exposing the mixture to a beam of interrogating white light along a second optical axis oriented about 60 degrees from the vertical axis of the test well and wherein the intensity of light passing through the incubated mixture is measured at an angle oriented about 30 degrees from the vertical axis of the test well.

7. The method of claim 6 wherein the intensity of light passing along the vertical axis of the test well is used to calculate the turbidity of the incubated mixture.

8. The method of claim 1 wherein the beam of interrogating white light is generated by at least one LED.

9. The method of claim 6 wherein the beam of interrogating white light is generated by at least one LED.

10. A microbiological analyzer perform microbiological tests on samples suspected of containing a microbial agent, the analyzer comprising:

a mechanism to hold a test well having a vertical axis aligned with the vertical axis of the measurement system;

a light source for directing interrogating white light along a first optical axis aligned with the vertical axis of the test well;

color filters for filtering the light passing through the test well about the first optical axis;

and sensors for measuring the hue, saturation, and intensity of the color filtered light about the first optical axis, in order to determine the color of the incubated mixture.

11. The analyzer of claim 10 wherein the color filters for filtering the light comprise red, green and blue filters.

12. The analyzer of claim 10 wherein measuring the intensity of the color filtered light comprises dividing the test well into a plurality of pixels, measuring the filtered intensity for each pixel.

13. The analyzer of claim 12 further comprising a computer programmed to calculate the hue, saturation, and intensity of each pixel of the incubated mixture from the measured intensities and accumulate into a histogram or average to arrive at a single hue, saturation and intensity, so that the identity of a microbial agent within the sample may be determined.

14. The analyzer of claim 10 further comprising a light source for exposing the mixture to a beam of interrogating white light along a second optical axis oriented about 60 degrees from the vertical axis of the test well.

15. The analyzer of claim 14 further comprising sensors adapted to measure the intensity of light passing through the incubated mixture about 30 degrees relative to the vertical axis of the test well is used to calculate the turbidity of the incubated mixture intensity.

16. The analyzer of claim 10 wherein the first light source comprises at least one LED.

17. The analyzer of claim 14 wherein the second light source comprises at least one LED.

* * * * *